United States Patent
King et al.

(10) Patent No.: US 11,957,931 B2
(45) Date of Patent: Apr. 16, 2024

(54) COMPOSITIONS AND METHODS FOR TREATING VITILIGO

(71) Applicants: YALE UNIVERSITY, New Haven, CT (US); UNIVERSITY OF MASSACHUSETTS, Boston, MA (US)

(72) Inventors: Brett King, Fairfield, CT (US); John E. Harris, Sterling, MA (US)

(73) Assignees: YALE UNIVERSITY, New Haven, CT (US); UNIVERSITY OF MASSACHUSETTS, Boston, MA (US)

(*) Notice: Subject to any disclaimer, the term of this patent is extended or adjusted under 35 U.S.C. 154(b) by 650 days.

(21) Appl. No.: 16/608,087

(22) PCT Filed: Apr. 26, 2018

(86) PCT No.: PCT/US2018/029531
§ 371 (c)(1),
(2) Date: Oct. 24, 2019

(87) PCT Pub. No.: WO2018/200786
PCT Pub. Date: Nov. 1, 2018

(65) Prior Publication Data
US 2020/0069965 A1 Mar. 5, 2020

Related U.S. Application Data

(60) Provisional application No. 62/490,304, filed on Apr. 26, 2017.

(51) Int. Cl.
*A61N 5/06* (2006.01)
*A61K 9/00* (2006.01)
(Continued)

(52) U.S. Cl.
CPC .......... *A61N 5/0616* (2013.01); *A61K 9/0014* (2013.01); *A61K 9/0053* (2013.01);
(Continued)

(58) Field of Classification Search
CPC ........ A61N 5/06; A61N 5/0618; A61N 5/062; A61N 2005/0626; A61N 2005/0627;
(Continued)

(56) References Cited

U.S. PATENT DOCUMENTS 11,278,505 B2 * 3/2022 Richmond ............ A61K 31/137
2010/0298444 A1 * 11/2010 Díaz Alperi ........... A61N 5/062
514/679

(Continued)

FOREIGN PATENT DOCUMENTS

WO 2016083433 A1 6/2016

OTHER PUBLICATIONS

Graiglow et al., "Tofacitinib Citrate for the Treatment of Vitiligo: A Pathogenesis-Directed Therapy," JAMA Dermatol. Oct. 2015; 151(10) (Year: 2015).*

(Continued)

*Primary Examiner* — Ahmed M Farah
(74) *Attorney, Agent, or Firm* — Saul Ewing LLP; Kathryn Doyle; Domingos J. Silva

(57) ABSTRACT

In its various aspects and embodiments, the invention comprises a method for treating vitiligo in a patient comprising administering a composition comprising an effective amount of at least one Janus kinase inhibitor and phototherapy.

16 Claims, 6 Drawing Sheets

Specification includes a Sequence Listing.

(51) Int. Cl.
*A61K 31/519* (2006.01)
*A61P 17/00* (2006.01)

(52) U.S. Cl.
CPC ............ *A61K 31/519* (2013.01); *A61N 5/062* (2013.01); *A61P 17/00* (2018.01); *A61N 2005/0661* (2013.01)

(58) Field of Classification Search
CPC .... A61N 2005/0642; A61N 2005/0643; A61N 2005/0644; A61N 2005/0658; A61N 2005/0661; A61N 5/067; A61N 5/0616; A61K 41/0057; A61K 41/0061; A61K 41/0066; A61K 41/0071; A61K 41/0076; A61K 41/008; A61K 9/0014; A61K 9/0019; A61K 9/0021; A61K 9/0053; A61K 9/0056; A61P 17/00; A61P 17/02
USPC ................................ 607/88–91, 94; 128/898
See application file for complete search history.

(56) References Cited

U.S. PATENT DOCUMENTS

| | | | | |
|---|---|---|---|---|
| 2016/0158575 | A1* | 6/2016 | Levatter | A61N 5/0616 607/88 |
| 2018/0162856 | A1* | 6/2018 | Esteve Trias | A61P 17/00 |
| 2019/0002466 | A1* | 1/2019 | Thorarensen | A61P 21/00 |
| 2022/0305282 | A1* | 9/2022 | Rafaeli | A61K 31/506 |

OTHER PUBLICATIONS

Reich et al., "Effects of Narrow Band UVB (311 nm) Irradiation on Epidermal Cells," Int. J. Mol. Sci. 2013, 14 8456-8466 (Year: 2013).*

Rothstein et al., "Treatment of vitiligo with the topical Janus Kinase inhibitor ruxolitinib," J Am Acad Dermatol, vol. 76, No. 6 (Year: 2017).*

International Search Report and Written Opinion for PCT International Application No. PCT/US2018/029531 dated Jul. 13, 2018.

Craiglow , et al., "Tofacitinib Citrate for the Treatment of Vitiligo: A Pathogenesis-Directed Therapy", JAMA Dermatol. 151(10), Oct. 2015, 1110-1112.

Harris , et al., "Rapid skin repigmentation on oral ruxolitinib in a patient with coexistent vitiligo and alopecia areata (AA)", J Am Acad Dermatol. 74(2), Feb. 2016, 370-371.

Kanda , et al., "IL-18 enhances IFN-gamma-induced production of CXCL9, CXCL 10, and CXCL11 in human keratinocytes", Eur J Immunol. 37(2), Feb. 2007, 338-350.

Kim , et al., "Rapid Repigmentation of Vitiligo Using Tofacitinib Plus Low-Dose, Narrowband UV-B Phototherapy", JAMA Dermatol. 154(3), Mar. 2018, 370-371.

Levy , et al., "Treatment of recalcitrant atopic dermatitis with the oral Janus kinase inhibitor tofacitinib citrate", J Am Acad Dermatol. 73(3), Sep. 2015, 395-399.

Liu , et al., "Repigmentation in vitiligo using the Janus kinase inhibitor tofacitinib may require concomitant light exposure", J Am Acad Dermatol. 77(4), Oct. 2017, 675-682.

Manga , et al., "Recent advances in understanding vitiligo", F1000 Research 5 (F1000 Faculty Rev-2234), Sep. 2016, 1-9.

Rashighi , et al., "CXCL10 is critical for the progression and maintenance of depigmentation in a mouse model of vitiligo", Sci Transl Med. 6(223):223ra23, Feb. 2014.

Rothstein , et al., "Treatment of vitiligo with the topical Janus kinase inhibitor ruxolitinib", J Am Acad Dermatol. 76(6), Jun. 2017, 1054-1060.

* cited by examiner

SEQUENCE LISTING

```
<160> NUMBER OF SEQ ID NOS: 4

<210> SEQ ID NO 1
<211> LENGTH: 1154
<212> TYPE: PRT
<213> ORGANISM: Homo sapiens

<400> SEQUENCE: 1

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285
```

```
Ser Met Leu Leu Ile Ser Ser Glu Asn Glu Met Asn Trp Phe His Ser
    290             295             300
Asn Asp Gly Gly Asn Val Leu Tyr Tyr Glu Val Met Val Thr Gly Asn
305             310             315             320
Leu Gly Ile Gln Trp Arg His Lys Pro Asn Val Val Ser Val Glu Lys
            325             330             335
Glu Lys Asn Lys Leu Lys Arg Lys Lys Leu Glu Asn Lys His Lys Lys
        340             345             350
Asp Glu Glu Lys Asn Lys Ile Arg Glu Glu Trp Asn Asn Phe Ser Tyr
    355             360             365
Phe Pro Glu Ile Thr His Ile Val Ile Lys Ser Val Val Ser Ile
370             375             380
Asn Lys Gln Asp Asn Lys Lys Met Glu Leu Lys Leu Ser Ser His Glu
385             390             395             400
Glu Ala Leu Ser Phe Val Ser Leu Val Asp Gly Tyr Phe Arg Leu Thr
            405             410             415
Ala Asp Ala His His Tyr Leu Cys Thr Asp Val Ala Pro Pro Leu Ile
        420             425             430
Val His Asn Ile Gln Asn Gly Cys His Gly Pro Ile Cys Thr Glu Tyr
    435             440             445
Ala Ile Asn Lys Leu Arg Gln Glu Gly Ser Glu Gly Met Tyr Val
450             455             460
Leu Arg Trp Ser Cys Thr Asp Phe Asp Asn Ile Leu Met Thr Val Thr
465             470             475             480
Cys Phe Glu Lys Ser Glu Gln Val Gln Gly Ala Gln Lys Gln Phe Lys
            485             490             495
Asn Phe Gln Ile Glu Val Gln Lys Gly Arg Tyr Ser Leu His Gly Ser
        500             505             510
Asp Arg Ser Phe Pro Ser Leu Gly Asp Leu Met Ser His Leu Lys Lys
    515             520             525
Gln Ile Leu Arg Thr Asp Asn Ile Ser Phe Met Leu Lys Arg Cys Cys
530             535             540
Gln Pro Lys Pro Arg Glu Ile Ser Asn Leu Leu Val Ala Thr Lys Lys
545             550             555             560
Ala Gln Glu Trp Gln Pro Val Tyr Pro Met Ser Gln Leu Ser Phe Asp
            565             570             575
Arg Ile Leu Lys Lys Asp Leu Val Gln Gly Glu His Leu Gly Arg Gly
        580             585             590
Thr Arg Thr His Ile Tyr Ser Gly Thr Leu Met Asp Tyr Lys Asp Asp
    595             600             605
Glu Gly Thr Ser Glu Glu Lys Lys Ile Lys Val Ile Leu Lys Val Leu
610             615             620
Asp Pro Ser His Arg Asp Ile Ser Leu Ala Phe Phe Glu Ala Ala Ser
625             630             635             640
Met Met Arg Gln Val Ser His Lys His Ile Val Tyr Leu Tyr Gly Val
            645             650             655
Cys Val Arg Asp Val Glu Asn Ile Met Val Glu Phe Val Glu Gly
        660             665             670
Gly Pro Leu Asp Leu Phe Met His Arg Lys Ser Asp Val Leu Thr Thr
    675             680             685
Pro Trp Lys Phe Lys Val Ala Lys Gln Leu Ala Ser Ala Leu Ser Tyr
690             695             700
```

```
Leu Glu Asp Lys Asp Leu Val His Gly Asn Val Cys Thr Lys Asn Leu
705                 710                 715                 720

Leu Leu Ala Arg Glu Gly Ile Asp Ser Glu Cys Gly Pro Phe Ile Lys
            725                 730                 735

Leu Ser Asp Pro Gly Ile Pro Ile Thr Val Leu Ser Arg Gln Glu Cys
        740                 745                 750

Ile Glu Arg Ile Pro Trp Ile Ala Pro Glu Cys Val Glu Asp Ser Lys
    755                 760                 765

Asn Leu Ser Val Ala Ala Asp Lys Trp Ser Phe Gly Thr Thr Leu Trp
770                 775                 780

Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
        835                 840                 845

Glu Glu Gln Asn Pro Asp Ile Val Ser Glu Lys Lys Pro Ala Thr Glu
850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
        915                 920                 925

Leu Arg Asn Leu Tyr His Glu Asn Ile Val Lys Tyr Lys Gly Ile Cys
930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
            980                 985                 990

Tyr Leu Gly Ser Arg Gln Tyr Val His Arg Asp Leu Ala Ala Arg Asn
        995                 1000                1005

Val Leu Val Glu Ser Glu His Gln Val Lys Ile Gly Asp Phe Gly
    1010                1015                1020

Leu Thr Lys Ala Ile Glu Thr Asp Lys Glu Tyr Tyr Thr Val Lys
    1025                1030                1035

Asp Asp Arg Asp Ser Pro Val Phe Trp Tyr Ala Pro Glu Cys Leu
    1040                1045                1050

Met Gln Ser Lys Phe Tyr Ile Ala Ser Asp Val Trp Ser Phe Gly
    1055                1060                1065

Val Thr Leu His Glu Leu Leu Thr Tyr Cys Asp Ser Asp Ser Ser
    1070                1075                1080

Pro Met Ala Leu Phe Leu Lys Met Ile Gly Pro Thr His Gly Gln
    1085                1090                1095

Met Thr Val Thr Arg Leu Val Asn Thr Leu Lys Glu Gly Lys Arg
    1100                1105                1110
```

```
Leu Pro Cys Pro Pro Asn Cys Pro Asp Glu Val Tyr Gln Leu Met
    1115                1120                1125

Arg Lys Cys Trp Glu Phe Gln Pro Ser Asn Arg Thr Ser Phe Gln
    1130                1135                1140

Asn Leu Ile Glu Gly Phe Glu Ala Leu Leu Lys
    1145                1150

<210> SEQ ID NO 2
<211> LENGTH: 1132
<212> TYPE: PRT
<213> ORGANISM: Homo sapiens

<400> SEQUENCE: 2

Met Gly Met Ala Cys Leu Thr Met Thr Glu Met Gly Thr Ser Thr
1               5                   10                  15

Ser Ser Ile Tyr Gln Asn Gly Asp Ile Ser Gly Asn Ala Asn Ser Met
                20                  25                  30

Lys Gln Ile Asp Pro Val Leu Gln Val Tyr Leu Tyr His Ser Leu Gly
                35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
                100                 105                 110

Leu Tyr Arg Ile Arg Phe Tyr Phe Pro Arg Trp Tyr Cys Ser Gly Ser
                115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
                180                 185                 190

Asn Asp Gln Thr Pro Leu Ala Ile Tyr Asn Ser Ile Ser Tyr Lys Thr
    195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
                260                 265                 270

Lys Glu Pro Gly Ser Gly Pro Ser Gly Glu Glu Ile Phe Ala Thr Ile
            275                 280                 285

Ile Ile Thr Gly Asn Gly Gly Ile Gln Trp Ser Arg Gly Lys His Lys
            290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335
```

-continued

```
Asn Glu Ser Arg Val Val Thr Ile His Lys Gln Asp Gly Lys Asn Leu
                340                 345                 350
Glu Ile Glu Leu Ser Ser Leu Arg Glu Ala Leu Ser Phe Val Ser Leu
            355                 360                 365
Ile Asp Gly Tyr Tyr Arg Leu Thr Ala Asp Ala His His Tyr Leu Cys
        370                 375                 380
Lys Glu Val Ala Pro Pro Ala Val Leu Glu Asn Ile Gln Ser Asn Cys
385                 390                 395                 400
His Gly Pro Ile Ser Met Asp Phe Ala Ile Ser Lys Leu Lys Lys Ala
                405                 410                 415
Gly Asn Gln Thr Gly Leu Tyr Val Leu Arg Cys Ser Pro Lys Asp Phe
            420                 425                 430
Asn Lys Tyr Phe Leu Thr Phe Ala Val Glu Arg Glu Asn Val Ile Glu
        435                 440                 445
Tyr Lys His Cys Leu Ile Thr Lys Asn Glu Asn Glu Glu Tyr Asn Leu
    450                 455                 460
Ser Gly Thr Lys Lys Asn Phe Ser Ser Leu Lys Asp Leu Leu Asn Cys
465                 470                 475                 480
Tyr Gln Met Glu Thr Val Arg Ser Asp Asn Ile Ile Phe Gln Phe Thr
                485                 490                 495
Lys Cys Cys Pro Pro Lys Pro Lys Asp Lys Ser Asn Leu Leu Val Phe
            500                 505                 510
Arg Thr Asn Gly Val Ser Asp Val Pro Thr Ser Pro Thr Leu Gln Arg
        515                 520                 525
Pro Thr His Met Asn Gln Met Val Phe His Lys Ile Arg Asn Glu Asp
    530                 535                 540
Leu Ile Phe Asn Glu Ser Leu Gly Gln Gly Thr Phe Thr Lys Ile Phe
545                 550                 555                 560
Lys Gly Val Arg Arg Glu Val Gly Asp Tyr Gly Gln Leu His Glu Thr
                565                 570                 575
Glu Val Leu Leu Lys Val Leu Asp Lys Ala His Arg Asn Tyr Ser Glu
            580                 585                 590
Ser Phe Phe Glu Ala Ala Ser Met Met Ser Lys Leu Ser His Lys His
        595                 600                 605
Leu Val Leu Asn Tyr Gly Val Cys Val Cys Gly Asp Glu Asn Ile Leu
    610                 615                 620
Val Gln Glu Phe Val Lys Phe Gly Ser Leu Asp Thr Tyr Leu Lys Lys
625                 630                 635                 640
Asn Lys Asn Cys Ile Asn Ile Leu Trp Lys Leu Glu Val Ala Lys Gln
                645                 650                 655
Leu Ala Trp Ala Met His Phe Leu Glu Glu Asn Thr Leu Ile His Gly
            660                 665                 670
Asn Val Cys Ala Lys Asn Ile Leu Leu Ile Arg Glu Glu Asp Arg Lys
        675                 680                 685
Thr Gly Asn Pro Pro Phe Ile Lys Leu Ser Asp Pro Gly Ile Ser Ile
    690                 695                 700
Thr Val Leu Pro Lys Asp Ile Leu Gln Glu Arg Ile Pro Trp Val Pro
705                 710                 715                 720
Pro Glu Cys Ile Glu Asn Pro Lys Asn Leu Asn Leu Ala Thr Asp Lys
                725                 730                 735
Trp Ser Phe Gly Thr Thr Leu Trp Glu Ile Cys Ser Gly Gly Asp Lys
            740                 745                 750
```

```
Pro Leu Ser Ala Leu Asp Ser Gln Arg Lys Leu Gln Phe Tyr Glu Asp
            755                 760                 765

Arg His Gln Leu Pro Ala Pro Lys Trp Ala Glu Leu Ala Asn Leu Ile
    770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
            820                 825                 830

Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
    850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val  Leu Pro Gln Asp Lys  Glu Tyr Tyr
        995                 1000                1005

Lys Val  Lys Glu Pro Gly Glu  Ser Pro Ile Phe Trp  Tyr Ala Pro
    1010                1015                1020

Glu Ser  Leu Thr Glu Ser Lys  Phe Ser Val Ala Ser  Asp Val Trp
    1025                1030                1035

Ser Phe  Gly Val Val Leu Tyr  Glu Leu Phe Thr Tyr  Ile Glu Lys
    1040                1045                1050

Ser Lys  Ser Pro Pro Ala Glu  Phe Met Arg Met Ile  Gly Asn Asp
    1055                1060                1065

Lys Gln  Gly Gln Met Ile Val  Phe His Leu Ile Glu  Leu Leu Lys
    1070                1075                1080

Asn Asn  Gly Arg Leu Pro Arg  Pro Asp Gly Cys Pro  Asp Glu Ile
    1085                1090                1095

Tyr Met  Ile Met Thr Glu Cys  Trp Asn Asn Asn Val  Asn Gln Arg
    1100                1105                1110

Pro Ser  Phe Arg Asp Leu Ala  Leu Arg Val Asp Gln  Ile Arg Asp
    1115                1120                1125

Asn Met  Ala Gly
    1130
```

```
<210> SEQ ID NO 3
<211> LENGTH: 1124
<212> TYPE: PRT
<213> ORGANISM: Homo sapiens

<400> SEQUENCE: 3

Met Ala Pro Pro Ser Glu Glu Thr Pro Leu Ile Pro Gln Arg Ser Cys
 1               5                  10                  15

Ser Leu Leu Ser Thr Glu Ala Gly Ala Leu His Val Leu Leu Pro Ala
                20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Gly Ile Leu
        50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
            115                 120                 125

Leu Asp Leu Pro Val Leu Glu His Leu Phe Ala Gln His Arg Ser Asp
        130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
290                 295                 300

Gln Ala Pro Arg Val Gly Pro Ala Gly Glu His Arg Leu Val Thr Val
                305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
            340                 345                 350

Thr Asp Ser Gln His Phe Phe Cys Lys Glu Val Ala Pro Pro Arg Leu
        355                 360                 365

Leu Glu Glu Val Ala Glu Gln Cys His Gly Pro Ile Thr Leu Asp Phe
370                 375                 380
```

```
Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
            405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
            435                 440                 445

Ser Leu Arg Glu Leu Leu Ala Thr Cys Trp Asp Gly Leu His Val
    450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
            485                 490                 495

Ser Ser Leu Val Gln Pro Gln Ser Gln Tyr Gln Leu Ser Gln Met Thr
            500                 505                 510

Phe His Lys Ile Pro Ala Asp Ser Leu Glu Trp His Glu Asn Leu Gly
    515                 520                 525

His Gly Ser Phe Thr Lys Ile Tyr Arg Gly Cys Arg His Glu Val Val
    530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
            595                 600                 605

Asp Met Tyr Leu Arg Lys Arg Gly His Leu Val Pro Ala Ser Trp Lys
            610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
            675                 680                 685

Pro Trp Val Ala Pro Glu Cys Leu Arg Glu Ala Gln Thr Leu Ser Leu
            690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
                725                 730                 735

Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
    770                 775                 780

Tyr Glu Leu Leu Ser Asp Pro Thr Pro Gly Ala Leu Ala Pro Arg Asp
785                 790                 795                 800
```

-continued

Gly Leu Trp Asn Gly Ala Gln Leu Tyr Ala Cys Gln Asp Pro Thr Ile
            805                 810                 815

Phe Glu Glu Arg His Leu Lys Tyr Ile Ser Gln Leu Gly Lys Gly Asn
        820                 825                 830

Phe Gly Ser Val Glu Leu Cys Arg Tyr Asp Pro Leu Gly Asp Asn Thr
    835                 840                 845

Gly Ala Leu Val Ala Val Lys Gln Leu Gln His Ser Gly Pro Asp Gln
850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
        915                 920                 925

Tyr Ser Ser Gln Ile Cys Lys Gly Met Glu Tyr Leu Gly Ser Arg Arg
    930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
        995                 1000                1005

Asp Val Trp Ser Phe Gly Val Val Leu Tyr Glu Leu Phe Thr Tyr
    1010                1015                1020

Cys Asp Lys Ser Cys Ser Pro Ser Ala Glu Phe Leu Arg Met Met
1025                1030                1035

Gly Cys Glu Arg Asp Val Pro Ala Leu Cys Arg Leu Leu Glu Leu
    1040                1045                1050

Leu Glu Glu Gly Gln Arg Leu Pro Ala Pro Pro Ala Cys Pro Ala
    1055                1060                1065

Glu Val His Glu Leu Met Lys Leu Cys Trp Ala Pro Ser Pro Gln
    1070                1075                1080

Asp Arg Pro Ser Phe Ser Ala Leu Gly Pro Gln Leu Asp Met Leu
    1085                1090                1095

Trp Ser Gly Ser Arg Gly Cys Glu Thr His Ala Phe Thr Ala His
    1100                1105                1110

Pro Glu Gly Lys His His Ser Leu Ser Phe Ser
    1115                1120

<210> SEQ ID NO 4
<211> LENGTH: 1187
<212> TYPE: PRT
<213> ORGANISM: Homo sapiens

<400> SEQUENCE: 4

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

```
Ser Ser Leu Thr Ala Glu Glu Val Cys Ile His Ile Ala His Lys Val
    50              55                  60

Gly Ile Thr Pro Pro Cys Phe Asn Leu Phe Ala Leu Phe Asp Ala Gln
65              70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
                100                 105                 110

His Gly Met Asn Pro Arg Glu Pro Ala Val Tyr Arg Cys Gly Pro Pro
            115                 120                 125

Gly Thr Glu Ala Ser Ser Asp Gln Thr Ala Gln Gly Met Gln Leu Leu
130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
                165                 170                 175

His His Phe Lys Asn Glu Ser Leu Gly Met Ala Phe Leu His Leu Cys
            180                 185                 190

His Leu Ala Leu Arg His Gly Ile Pro Leu Glu Glu Val Ala Lys Lys
            195                 200                 205

Thr Ser Phe Lys Asp Cys Ile Pro Arg Ser Phe Arg Arg His Ile Arg
210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
                260                 265                 270

Glu Arg Val Pro Val Cys His Leu Arg Leu Leu Ala Gln Ala Glu Gly
            275                 280                 285

Glu Pro Cys Tyr Ile Arg Asp Ser Gly Val Ala Pro Thr Asp Pro Gly
            290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
            355                 360                 365

Pro Arg Glu Pro Leu Trp Ala Tyr Phe Cys Asp Phe Arg Asp Ile Thr
            370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
                405                 410                 415

Val Ser Leu Val Asp Gly Tyr Phe Arg Leu Thr Ala Asp Ser Ser His
                420                 425                 430

Tyr Leu Cys His Glu Val Ala Pro Pro Arg Leu Val Met Ser Ile Arg
            435                 440                 445

Asp Gly Ile His Gly Pro Leu Leu Glu Pro Phe Val Gln Ala Lys Leu
450                 455                 460
```

```
Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
            485                 490                 495

Met Gln Ser Leu Arg Leu Arg Lys Phe Pro Ile Glu Gln Gln Asp Gly
        500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
        530                 535                 540

Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
            660                 665                 670

Val His Gly Val Cys Val Arg Gly Pro Glu Asn Ile Met Val Thr Glu
        675                 680                 685

Tyr Val Glu His Gly Pro Leu Asp Val Trp Leu Arg Arg Glu Arg Gly
    690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
            740                 745                 750

Pro Phe Ile Lys Leu Ser Asp Pro Gly Val Gly Leu Gly Ala Leu Ser
        755                 760                 765

Arg Glu Glu Arg Val Glu Arg Ile Pro Trp Leu Ala Pro Glu Cys Leu
    770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
    850                 855                 860

Asp Leu Thr Arg Leu Gln Pro His Asn Leu Ala Asp Val Leu Thr Val
865                 870                 875                 880
```

-continued

```
Asn Pro Asp Ser Pro Ala Ser Asp Pro Thr Val Phe His Lys Arg Tyr
            885             890              895
Leu Lys Lys Ile Arg Asp Leu Gly Glu Gly His Phe Gly Lys Val Ser
            900             905             910
Leu Tyr Cys Tyr Asp Pro Thr Asn Asp Gly Thr Gly Glu Met Val Ala
            915             920             925
Val Lys Ala Leu Lys Ala Asp Cys Gly Pro Gln His Arg Ser Gly Trp
            930             935         940
Lys Gln Glu Ile Asp Ile Leu Arg Thr Leu Tyr His Glu His Ile Ile
945                 950             955                 960
Lys Tyr Lys Gly Cys Cys Glu Asp Gln Gly Glu Lys Ser Leu Gln Leu
                965             970             975
Val Met Glu Tyr Val Pro Leu Gly Ser Leu Arg Asp Tyr Leu Pro Arg
            980             985             990
His Ser Ile Gly Leu Ala Gln Leu  Leu Leu Phe Ala Gln  Gln Ile Cys
        995         1000                 1005
Glu Gly Met Ala Tyr Leu His  Ala Gln His Tyr Ile  His Arg Asp
        1010            1015            1020
Leu Ala Ala Arg Asn Val Leu  Leu Asp Asn Asp Arg  Leu Val Lys
        1025            1030            1035
Ile Gly Asp Phe Gly Leu Ala  Lys Ala Val Pro Glu  Gly His Glu
        1040            1045            1050
Tyr Tyr Arg Val Arg Glu Asp  Gly Asp Ser Pro Val  Phe Trp Tyr
        1055            1060            1065
Ala Pro Glu Cys Leu Lys Glu  Tyr Lys Phe Tyr Tyr  Ala Ser Asp
        1070            1075            1080
Val Trp Ser Phe Gly Val Thr  Leu Tyr Glu Leu Leu  Thr His Cys
        1085            1090            1095
Asp Ser Ser Gln Ser Pro Pro  Thr Lys Phe Leu Glu  Leu Ile Gly
        1100            1105            1110
Ile Ala Gln Gly Gln Met Thr  Val Leu Arg Leu Thr  Glu Leu Leu
        1115            1120            1125
Glu Arg Gly Glu Arg Leu Pro  Arg Pro Asp Lys Cys  Pro Cys Glu
        1130            1135            1140
Val Tyr His Leu Met Lys Asn  Cys Trp Glu Thr Glu  Ala Ser Phe
        1145            1150            1155
Arg Pro Thr Phe Glu Asn Leu  Ile Pro Ile Leu Lys  Thr Val His
        1160            1165            1170
Glu Lys Tyr Gln Gly Gln Ala  Pro Ser Val Phe Ser  Val Cys
        1175            1180            1185
```

US 11,957,931 B2

COMPOSITIONS AND METHODS FOR TREATING VITILIGO

CROSS-REFERENCE TO RELATED APPLICATIONS

This present application is a 35 U.S.C. § 371 national phase application from, and claims priority to, International Application No. PCT/US2018/029531, filed Apr. 26, 2018, and published under PCT Article 21(2) in English, which claims priority under 35 U.S.C. § 119(e) to U.S. Provisional Application No. 62/490,304 filed Apr. 26, 2017, all of which applications are incorporated herein by reference in their entireties.

STATEMENT REGARDING FEDERALLY SPONSORED RESEARCH OR DEVELOPMENT

This invention was made with government support under TR001453 and AR069114 awarded by National Institutes of Health. The government has certain rights in the invention.

BACKGROUND OF THE INVENTION

Vitiligo is a chronic autoimmune disease that results from the destruction of melanocytes, causing white spots on the skin. Vitiligo affects approximately 1% of people worldwide and can affect both adults and children, causing diminished quality of life and marked psychological distress. The pathogenesis of vitiligo involves the destruction of melanocytes via cell mediated immunity, and studies show that IFN-γ and CD8⁻ T cells play a key role in this process.

Treatments for vitiligo include topical corticosteroids and calcineurin inhibitors, but the most effective treatment and mainstay of therapy is narrowband ultraviolet B (nbUVB) phototherapy. However, incomplete response to treatment is common.

Accordingly, there is a need in the art for methods and compositions that reduce the symptoms of vitiligo and reverse depigmentation in affected areas. Such methods and compositions should allow for maintenance of repigmentation in patients under treatment. The present disclosure addresses that need.

SUMMARY OF THE INVENTION

In one aspect, the invention provides a method for treating vitiligo in a subject. In another aspect, the invention provides a kit comprising an effective amount of at least one Janus kinase inhibitor.

In various embodiments, the method comprises administering a therapeutically effective amount of at least one Janus kinase inhibitor to the subject, wherein the subject is further administered phototherapy.

In various embodiments, the at least one Janus kinase inhibitor is selected from the group consisting of tofacitinib, ruxolitinib, oclacitinib, baricitinib, filgotinib, gandotinib, lestaurtinib, momelotinib, pacritinib, upadacitinib (ABT-494), peficitinib, cucurbitacin I, CHZ868, fedratinib, cerdulatinib, ATI-50001, Leo-124429, or a salt or solvate thereof.

In various embodiments, the at least one Janus kinase inhibitor is tofacitinib or a salt or solvate thereof In various embodiments, the subject is administered about 5-20 mg/day of tofacitinib.

In various embodiments, the at least one Janus kinase inhibitor is ruxolitinib or a salt or solvate thereof. In various embodiments, the subject is administered about 5-50 mg/day of ruxolitinib.

In various embodiments, the phototherapy comprises low-dose narrow band UVB phototherapy. In various embodiments, the phototherapy comprises a dose equal to or less than about 150 mJ/cm² of nbUVB. In various embodiments, the phototherapy comprises a dose equal to or greater than about 150 mJ/cm² of nbUVB. In various embodiments, the phototherapy is applied at least to the subject's skin section that is afflicted by vitiligo. In various embodiments, the phototherapy is substantially restricted to the subject's skin section that is afflicted by vitiligo. In various embodiments, the at least one Janus kinase inhibitor is administered topically.

In various embodiments, the intensity, duration and/or frequency of the phototherapy used is ineffective in treating vitiligo in a subject who is not being co-administered the at least one Janus kinase inhibitor. In various embodiments, the subject continues to be administered the at least one Janus kinase inhibitor after the phototherapy is discontinued.

In various embodiments, the at least one Janus kinase inhibitor is part of a pharmaceutical composition further comprising at least one pharmaceutically acceptable excipient. In various embodiments, the at least one Janus kinase inhibitor is administered orally or topically to the subject.

In various embodiments, the at least one Janus kinase inhibitor is the only agent that treats vitiligo that is administered to the subject. In various embodiments, the at least one Janus kinase inhibitor is the only agent that treats vitiligo that is administered to the subject in a therapeutically effective amount.

In various embodiments, the invention further provides instructional material comprising instructions for the concomitant administration of the at least one JAKi with phototherapy to treat vitiligo in a subject. In various embodiments, the kit further comprises a handheld phototherapy device.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A shows the sun-exposed forearm and dorsal hand, before and during treatment, and demonstrates repigmentation. FIG. 1B shows the chest, before and during treatment, under room light (top panels) and Wood's lamp (bottom panels), and demonstrates repigmentation of sun-exposed lesions involving the upper chest but not sun-protected lesions involving the intermammary chest.

FIG. 2A depicts representative CD8⁺ T cells in the CD8⁺ gate for each site at baseline and after treatment. CD8⁺ T cells were first gated on singlets and then by physical parameters SSC and FSC, all live cells, all CD45⁺ cells, all CD3⁺ cells and all CD8⁻ T cells. FIGS. 2B-2D show a comparison of CD8⁺ T cell number (FIG. 2B), CXCL9 (FIG. 2C) and CXCL10 (FIG. 2D) in each site before and after treatment. R=responding site, NR=Non-responding site, NL=non-lesional site.

FIG. 4A shows mart-1 Pentamter$^+$ CD8$^+$ T cells in the peripheral blood mononuclear cells (PBMCs) before and after treatment. Fluorescent minus-one samples are shown on the left, the full staining is shown on the right. FIG. 4B depicts CXCL9 and CXCL10 chemokine levels in the serum at baseline and post-treatment.

DETAILED DESCRIPTION OF THE INVENTION

Definitions

Figure 1B:
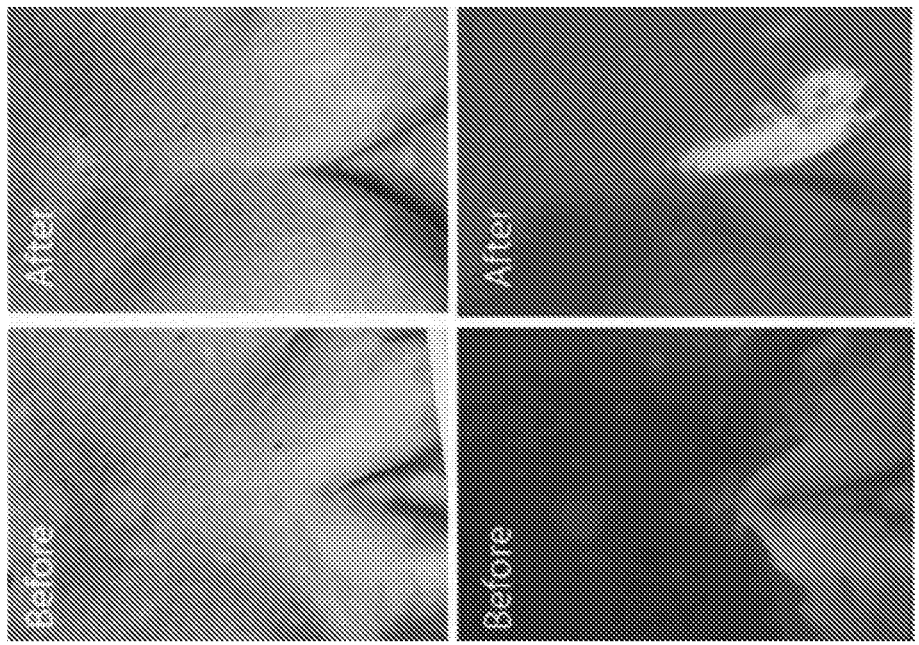
FIGS. 1A-1B depict clinical images of patient 1 in Example 1 with vitiligo.

The instant invention is most clearly understood with reference to the following definitions.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

The terms "biomarker" or "marker," as used herein, refers to a molecule that can be detected. Therefore, a biomarker according to the present invention includes, but is not limited to, a nucleic acid, polypeptide, carbohydrate, lipid, inorganic molecule, and/or organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "depigmentation" as used herein refers to any significant depletion of melanocytes and/or skin pigmentation in a specific area of skin due to vitiligo. In certain embodiments, depigmentation occurs due to complete or partial loss of melanocytes or their function.

The phrase "inhibit," as used herein, means to reduce a molecule, reaction, interaction, gene, mRNA, and/or protein's expression, stability, function or activity by a measurable amount or to prevent entirely. Inhibitors are compounds that, e.g., bind to, partially or totally block stimulation, decrease, prevent, delay activation, inactivate, desensitize, or downregulate a protein, a gene, and an mRNA stability, expression, function and activity, e.g., antagonists.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "isolated," "purified," or "biologically pure" refer to material that is free to varying degrees from components that normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein "Janus kinase" or "JAK" means a member of the tyrosine kinase family of genes or proteins that are important for cytokine signaling.

By "Janus kinase 1" or "Janus kinase type 1" or "JAK1" is meant the member of the JAK family having the following sequence for the human polypeptide, SEQ ID NO: 1

```
        10         20         30         40
MQYLNIKEDC NAMAFCAKMR SSKKTEVNLE APEPGVEVIF 50         60         70         80
YLSDREPLRL GSGEYTAEEL CIRAAQACRI SPLCHNLFAL 90        100        110        120
YDENTKLWYA PNRTITVDDK MSLRLHYRMR FYFTNWHGTN 130        140        150        160
DNEQSVWRHS PKKQKNGYEK KKIPDATPLL DASSLEYLFA 170        180        190        200
QGQYDLVKCL APIRDPKTEQ DGHDIENECL GMAVLAISHY 210        220        230        240
AMMKKMQLPE LPKDISYKRY IPETLNKSIR QRNLLTRMRI 250        260        270        280
NNVFKDFLKE FNNKTICDSS VSTHDLKVKY LATLETLTKH 290        300        310        320
YGAEIFETSM LLISSENEMN WFHSNDGGNV LYYEVMVTGN
```

-continued
```
       330        340        350        360
LGIQWRHKPN VVSVEKEKNK LKRKKLENKH KKDEEKNKIR 370        380        390        400
EEWNNFSYFP EITHIVIKES VVSINKQDNK KMELKLSSHE 410        420        430        440
EALSFVSLVD GYFRLTADAH HYLCTDVAPP LIVHNIQNGC 450        460        470        480
HGPICTEYAI NKLRQEGSEE GMYVLRWSCT DFDNILMTVT 490        500        510        520
CFEKSEQVQG AQKQFKNFQI EVQKGRYSLH GSDRSFPSLG 530        540        550        560
DLMSHLKKQI LRTDNISFML KRCCQPKPRE ISNLLVATKK 570        580        590        600
AQEWQPVYPM SQLSFDRILK KDLVQGEHLG RGTRTHIYSG 610        620        630        640
TLMDYKDDEG TSEEKKIKVI LKVLDPSHRD ISLAFFEAAS 650        660        670        680
MMRQVSHKHI VYLYGVCVRD VENIMVEEFV EGGPLDLFMH 690        700        710        720
RKSDVLTTPW KFKVAKQLAS ALSYLEDKDL VHGNVCTKNL 730        740        750        760
LLAREGIDSE CGPFIKLSDP GIPITVLSRQ ECIERIPWIA 770        780        790        800
PECVEDSKNL SVAADKWSFG TTLWEICYNG EIPLKDKTLI 810        820        830        840
EKERFYESRC RPVTPSCKEL ADLMTRCMNY DPNQRPFFRA 850        860        870        880
IMRDINKLEE QNPDIVSEKK PATEVDPTHF EKRFLKRIRD 890        900        910        920
LGEGHFGKVE LCRYDPEGDN TGEQVAVKSL KPESGGNHIA 930        940        950        960
DLKKEIEILR NLYHENIVKY KGICTEDGGN GIKLIMEFLP 970        980        990       1000
SGSLKEYLPK NKNKINLKQQ LKYAVQICKG MDYLGSRQYV 1010       1020       1030       1040
HRDLAARNVL VESEHQVKIG DFGLTKAIET DKEYYTVKDD 1050       1060       1070       1080
RDSPVFWYAP ECLMQSKFYI ASDVWSFGVT LHELLTYCDS 1090       1100       1110       1120
DSSPMALFLK MIGPTHGQMT VTRLVNTLKE GKRLPCPPNC 1130       1140       1150
PDEVYQLMRK CWEFQPSNRT SFQNLIEGFE ALLK
```

By "Janus kinase 2" or "Janus kinase type 2" or "JAK2" is meant the member of the JAK family having the following sequence for the human polypeptide, SEQ ID NO: 2

```
        10         20         30         40
MGMACLTMTE MEGTSTSSIY QNGDISGNAN SMKQIDPVLQ 50         60         70         80
VYLYHSLGKS EADYLTFPSG EYVAEEICIA ASKACGITPV 90        100        110        120
YHNMFALMSE TERIWYPPNH VFHIDESTRH NVLYRIRFYF 130        140        150        160
PRWYCSGSNR AYRHGISRGA EAPLLDDFVM SYLFAQWRHD
```

-continued

```
         170        180        190        200
  FVHGWIKVPV THETQEECLG MAVLDMMRIA KENDQTPLAI 210        220        230        240
  YNSISYKTFL PKCIRAKIQD YHILTRKRIR YRFRRFIQQF 250        260        270        280
  SQCKATARNL KLKYLINLET LQSAFYTEKF EVKEPGSGPS 290        300        310        320
  GEEIFATIII TGNGGIQWSR GKHKESETLT EQDLQLYCDF 330        340        350        360
  PNIIDVSIKQ ANQEGSNESR VVTIHKQDGK NLEIELSSLR 370        380        390        400
  EALSFVSLID GYYRLTADAH HYLCKEVAPP AVLENIQSNC 410        420        430        440
  HGPISMDFAI SKLKKAGNQT GLYVLRCSPK DFNKYFLTFA 450        460        470        480
  VERENVIEYK HCLITKNENE EYNLSGTKKN FSSLKDLLNC 490        500        510        520
  YQMETVRSDN IIFQFTKCCP PKPKDKSNLL VFRTNGVSDV 530        540        550        560
  PTSPTLQRPT HMNQMVFHKI RNEDLIFNES LGQGTFTKIF 570        580        590        600
  KGVRREVGDY GQLHETEVLL KVLDKAHRNY SESFFEAASM 610        620        630        640
  MSKLSHKHLV LNYGVCVCGD ENILVQEFVK FGSLDTYLKK 650        660        670        680
  NKNCINILWK LEVAKQLAWA MHFLEENTLI HGNVCAKNIL 690        700        710        720
  LIREEDRKTG NPPFIKLSDP GISITVLPKD ILQERIPWVP 730        740        750        760
  PECIENPKNL NLATDKWSFG TTLWEICSGG DKPLSALDSQ 770        780        790        800
  RKLQFYEDRH QLPAPKWAEL ANLINNCMDY EPDFRPSFRA 810        820        830        840
  IIRDLNSLFT PDYELLTEND MLPNMRIGAL GFSGAFEDRD 850        860        870        880
  PTQFEERHLK FLQQLGKGNF GSVEMCRYDP LQDNTGEVVA 890        900        910        920
  VKKLQHSTEE HLRDFEREIE ILKSLQHDNI VKYKGVCYSA 930        940        950        960
  GRRNLKLIME YLPYGSLRDY LQKHKERIDH IKLLQYTSQI 970        980        990       1000
  CKGMEYLGTK RYIHRDLATR NILVENENRV KIGDFGLTKV 1010       1020       1030       1040
  LPQDKEYYKV KEPGESPIFW YAPESLTESK FSVASDVWSF 1050       1060       1070       1080
  GVVLYELFTY IEKSKSPPAE FMRMIGNDKQ GQMIVFHLIE 1090       1100       1110       1120
  LLKNNGRLPR PDGCPDEIYM IMTECWNNNV NQRPSFRDLA

1130
  LRVDQIRDNM AG
```

By "Janus kinase 3" or "Janus kinase type 3" or "JAK3" is meant the member of the JAK family having the following sequence for the human polypeptide, SEQ ID NO: 3

```
         10         20         30         40
  MAPPSEETPL IPQRSCSLLS TEAGALHVLL PARGPGPPQR 50         60         70         80
  LSFSFGDHLA EDLCVQAAKA SGILPVYHSL FALATEDLSC 90        100        110        120
  WFPPSHIFSV EDASTQVLLY RIRFYFPNWF GLEKCHRFGL 130        140        150        160
  RKDLASAILD LPVLEHLFAQ HRSDLVSGRL PVGLSLKEQG 170        180        190        200
  ECLSLAVLDL ARMAREQAQR PGELLKTVSY KACLPPSLRD 210        220        230        240
  LIQGLSFVTR RRIRRTVRRA LRRVAACQAD RHSLMAKYIM 250        260        270        280
  DLERLDPAGA AETFHVGLPG ALGGHDGLGL LRVAGDGGIA 290        300        310        320
  WTQGEQEVLQ PFCDFPEIVD ISIKQAPRVG PAGEHRLVTV 330        340        350        360
  TRTDNQILEA EFPGLPEALS FVALVDGYFR LTTDSQHFFC 370        380        390        400
  KEVAPPRLLE EVAEQCHGPI TLDFAINKLK TGGSRPGSYV 410        420        430        440
  LRRSPQDFDS FLLTVCVQNP LGPDYKGCLI RRSPTGTFLL 450        460        470        480
  VGLSRPHSSL RELLATCWDG GLHVDGVAVT LTSCCIPRPK 490        500        510        520
  EKSNLIVVQR GHSPPTSSLV QPQSQYQLSQ MTFHKIPADS 530        540        550        560
  LEWHENLGHG SFTKIYRGCR HEVVDGEARK TEVLLKVMDA 570        580        590        600
  KHKNCMESFL EAASLMSQVS YRHLVLLHGV CMAGDSTMVQ 610        620        630        640
  EFVHLGAIDM YLRKRGHLVP ASWKLQVVKQ LAYALNYLED 650        660        670        680
  KGLPHGNVSA RKVLLAREGA DGSPPFIKLS DPGVSPAVLS 690        700        710        720
  LEMLTDRIPW VAPECLREAQ TLSLEADKWG FGATVWEVFS 730        740        750        760
  GVTMPISALD PAKKLQFYED RQQLPAPKWT ELALLIQQCM 770        780        790        800
  AYEPVQRPSF RAVIRDLNSL ISSDYELLSD PTPGALAPRD 810        820        830        840
  GLWNGAQLYA CQDPTIFEER HLKYISQLGK GNFGSVELCR 850        860        870        880
  YDPLGDNTGA LVAVKQLQHS GPDQQRDFQR EIQILKALHS 890        900        910        920
  DFIVKYRGVS YGPGRQSLRL VMEYLPSGCL RDFLQRHRAR 930        940        950        960
  LDASRLLLYS SQICKGMEYL GSRRCVHRDL AARNILVESE 970        980        990       1000
  AHVKIADFGL AKLLPLDKDY YVVREPGQSP IFWYAPESLS 1010       1020       1030       1040
  DNIFSRQSDV WSFGVVLYEL FTYCDKSCSP SAEFLRMMGC 1050       1060       1070       1080
  ERDVPALCRL LELLEEGQRL PAPPACPAEV HELMKLCWAP
```

```
             1090       1100       1110       1120
SPQDRPSFSA LGPQLDMLWS GSRGCETHAF TAHPEGKHHS

LSFS
```

As used herein, "tyrosine kinase 2" or "TYK2" is meant the member of the JAK family having the following sequence for the human polypeptide, SEQ ID NO: 4

```
             10         20         30         40
MPLRHWGMAR GSKPVGDGAQ PMAAMGGLKV LLHWAGPGGG 50         60         70         80
EPWVTFSESS LTAEEVCIHI AHKVGITPPC FNLFALFDAQ 90        100        110        120
AQVWLPPNHI LEIPRDASLM LYFRIRFYFR NWHGMNPREP 130        140        150        160
AVYRCGPPGT EASSDQTAQG MQLLDPASFE YLFEQGKHEF 170        180        190        200
VNDVASLWEL STEEEIHHFK NESLGMAFLH LCHLALRHGI 210        220        230        240
PLEEVAKKTS FKDCIPRSFR RHIRQHSALT RLRLRNVFRR 250        260        270        280
FLRDFQPGRL SQQMVMVKYL ATLERLAPRF GTERVPVCHL 290        300        310        320
RLLAQAEGEP CYIRDSGVAP TDPGPESAAG PPTHEVLVTG 330        340        350        360
TGGIQWWPVE EEVNKEEGSS GSSGRNPQAS LFGKKAKAHK 370        380        390        400
AVGQPADRPR EPLWAYFCDF RDITHVVLKE HCVSIHRQDN 410        420        430        440
KCLELSLPSR AAALSFVSLV DGYFRLTADS SHYLCHEVAP 450        460        470        480
PRLVMSIRDG IHGPLLEPFV QAKLRPEDGL YLIHWSTSHP 490        500        510        520
YRLILTVAQR SQAPDGMQSL RLRKFPIEQQ DGAFVLEGWG 530        540        550        560
RSFPSVRELG AALQGCLLRA GDDCFSLRRC CLPQPGETSN 570        580        590        600
LIIMRGARAS PRTLNLSQLS FHRVDQKEIT QLSHLGQGTR 610        620        630        640
TNVYEGRLRV EGSGDPEEGK MDDEDPLVPG RDRGQELRVV 650        660        670        680
LKVLDPSHHD IALAFYETAS LMSQVSHTHL AFVHGVCVRG 690        700        710        720
PENIMVTEYV EHGPLDVWLR RERGHVPMAW KMVVAQQLAS 730        740        750        760
ALSYLENKNL VHGNVCGRNI LLARLGLAEG TSPFIKLSDP 770        780        790        800
GVGLGALSRE ERVERIPWLA PECLPGGANS LSTAMDKWGF 810        820        830        840
GATLLEICFD GEAPLQSRSP SEKEHFYQRQ HRLPEPSCPQ 850        860        870        880
LATLTSQCLT YEPTQRPSFR TILRDLTRLQ PHNLADVLTV 890        900        910        920
NPDSPASDPT VFHKRYLKKI RDLGEGHFGK VSLYCYDPTN 930        940        950        960
DGTGEMVAVK ALKADCGPQH RSGWKQEIDI LRTLYHEHII 970        980        990       1000
KYKGCCEDQG EKSLQLVMEY VPLGSLRDYL PRHSIGLAQL 1010       1020       1030       1040
LLFAQQICEG MAYLHAQHYI HRDLAARNVL LDNDRLVKIG 1050       1060       1070       1080
DFGLAKAVPE GHEYYRVRED GDSPVFWYAP ECLKEYKFYY 1090       1100       1110       1120
ASDVWSFGVT LYELLTHCDS SQSPPTKFLE LIGIAQGQMT 1130       1140       1150       1160
VLRLTELLER GERLPRPDKC PCEVYHLMKN CWETEASFRP 1170       1180
TFENLIPILK TVHEKYQGQA PSVFSVC
```

As used herein, "microRNA" or "miRNA" describes small non-coding RNA molecules, generally about 15 to about 50 nucleotides in length, preferably 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA), which are derived from primary transcripts (pri-miRNA) through sequential cleavage by RNAse III enzymes. miRBase is a comprehensive microRNA database located at www dot mirbase dot org, incorporated by reference herein in its entirety for all purposes.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

Unless specifically stated or obvious from context, the term "or" as used herein is understood to be inclusive.

As used herein, the term "pharmaceutical composition" or "composition" refers to a mixture of at least one compound and/or composition useful within the invention with a pharmaceutically acceptable carrier. The pharmaceutical composition facilitates administration of the compound and/or composition to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound and/or composition useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound and/or composition useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound and/or composition useful within the invention, and are physiologically acceptable to the patient. Supplementary active compounds may also be incorporated into the compositions. The "pharmaceutically acceptable carrier" may further include a pharmaceutically acceptable salt of the compound and/or composition useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound and/or composition prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds and/or compositions of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound and/or composition by reacting, for example, the appropriate acid or base with the compound and/or composition.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation. By "pharmaceutical formulation" it is further meant that the carrier, solvent, excipient(s) and/or salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

The term "phototherapy" as used herein refers to controlled and/or prescribed application of light to an area of or the entire body of a patient in order to derive a therapeutic benefit. Deliberate exposure of the body to sunlight is within the scope of this term, however exposure to light occurring during the course of ordinary life is not.

As used herein, "polynucleotide" includes cDNA, RNA, DNA/RNA hybrid, antisense RNA, siRNA, miRNA, snoRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, the term "prevent," "prevention," or "preventing" refers to any method to partially or completely prevent or delay the onset, worsening, and/or recurrence of one or more symptoms or features of a disease, disorder, and/or condition. Prevention is causing the clinical symptoms of the disease state not to develop, worsen, and/or recur, i.e., inhibiting the onset, spread, and/or recurrence of disease, in a subject that may be exposed to or predisposed to the disease state or that has been successfully treated already, but does not yet experience or display symptoms of the disease state. Prevention may be administered to a subject who does not exhibit signs or symptoms of a disease, disorder, and/or condition.

By "reduces" is meant a negative alteration of at least 10%, 25%, 50%, 75%, or 100%.

The term "repigmentation" as used herein refers to any significant replenishment of melanocytes and/or skin pigmentation in a specific area of skin. In certain embodiments, repigmentation occurs due to generation of functional melanocytes.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant an agent that recognizes and binds a polypeptide or polynucleotide of the invention, but which does not substantially recognize and bind other molecules in a sample, for example, a biological sample, which naturally includes a polynucleotide of the invention. In some embodiments, the agent is a nucleic acid molecule.

As used herein, the term "subject," "patient" or "individual" to which administration is contemplated includes, but is not limited to, humans (i.e., a male or female of any age group, e.g., a pediatric subject (e g , infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound and/or composition of the invention, that when administered to a patient, treats, minimizes and/or ameliorates a symptom of the disease or disorder. The amount of a compound and/or composition of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a compound and/or composition of the present invention, for example, a subject afflicted with a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

As used herein, the terms "ultraviolet light" or "UV" refers to light with a wavelength between 10 and 400 nm, including but not limited to, ultraviolet B (UVB, 280-320 nm) and ultraviolet A (UVA, 320-400 nm) and narrow regions thereof, e.g., narrowband ultraviolet B (nbUVB, 311-312 nm) and UVA1 (340-400 nm), with any intensity or from any source, including a manufactured device or the sun.

As used herein, the term "vitiligo" refers to the autoimmune disease associated with loss of functional melanocytes resulting in loss of pigment in circumscribed and/or diffuse areas of the skin.

Selected abbreviations used herein include: nbUVB, narrowband ultraviolet B; IFN-γ, Interferon-γ; AA, alopecia areata; JAK, Janus kinase; TYK, tyrosine kinase; BSA, body surface area; SD, standard deviation; C-X-C, motif chemokine ligand, CXCL; PBMCs, peripheral blood mononuclear cells.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In one aspect, the invention comprises a method for treating vitiligo in a subject. In certain embodiments, the method comprises administering at least one Janus kinase inhibitor (JAKi) to the subject, wherein the subject is further administered phototherapy. In other embodiments, the administration of the at least one JAKi and phototherapy is initially approximately contemporaneous. In other embodiments, after at least partial repigmentation is achieved, phototherapy is discontinued. In yet other embodiments, after at least partial repigmentation is achieved, administration of the at least one JAKi continues in order to maintain pigmentation. In yet other embodiments, the method reduces the area of depigmentation.

The pathogenesis of vitiligo involves $CD8^+$ T cell production of IFN-γ, which leads to CXCL9/10 expression by keratinocytes and further recruitment of $CD8^-$ T cells, resulting in melanocyte destruction. As reported herein, treatment with tofacitinib only led to repigmentation when there was concomitant light exposure, either sunlight or nbUVB phototherapy. The low doses of nbUVB that were beneficial would not typically be effective as monotherapy in vitiligo. Adverse events were mild and infrequent.

Without wishing to be bound by any particular theory, treatment of vitiligo with JAKi's appears to require light exposure, which can be relatively low in intensity, such as regular exposure to sunlight.

Figure 3:
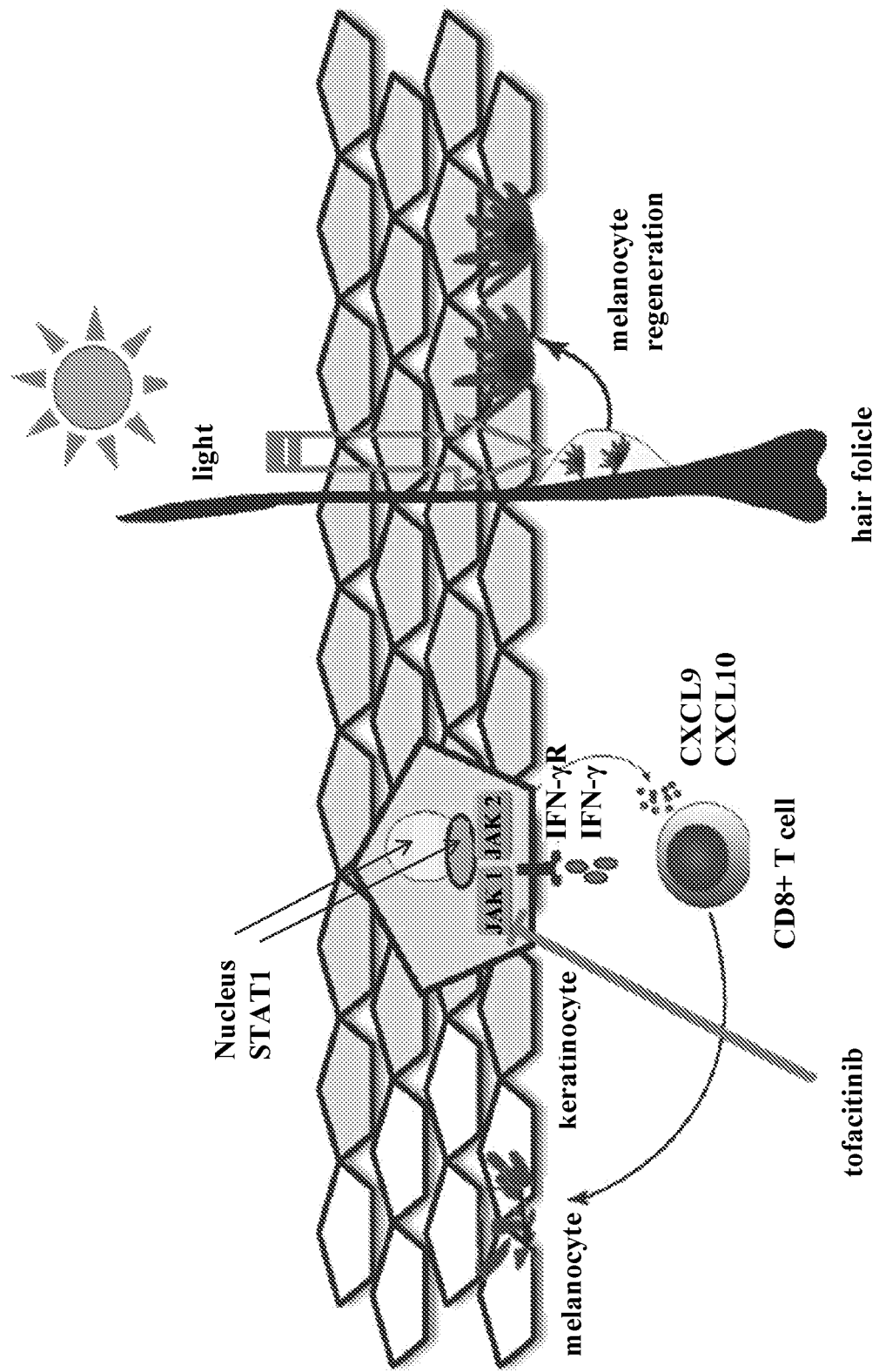
FIG. 3 depicts a model of vitiligo treatment with JAK inhibitor plus light exposure. Interferon (IFN)-γ signals through the IFN-γ Receptor (IFN-γR) via Janus kinase (JAK) 1 and JAK2, initiating phosphorylation of Signal Transducer and Activator of Transcription 1 (STAT1) and translocation to the nucleus where IFN-γ dependent genes, including C-X-C motif chemokine ligand (CXCL) 9 and CXCL10 are transcribed. CXCL9 and CXCL10 recruit autoreactive CD8$^+$ T cells to the skin where they attack melanocytes, leading to depigmentation (white keratinocytes). Tofacitinib inhibits this process by blocking JAK signaling. Even under JAK inhibitor suppression of vitiligo, regimentation depends on photoactivation to stimulate melanocytes to leave their stem cell niche in the hair follicle bulge and seed the epidermis to make pigment.

The model shown in FIG. 3 summarizes a non-limiting mechanism by which treatment with JAKi's combined with phototherapy promotes repigmentation in areas affected by vitiligo. Repigmentation requires both suppression of inflammation in the skin, which is achieved with JAK inhibitor treatment, and melanocyte stimulation via light exposure, which is most effectively accomplished by phototherapy. In certain non-limiting embodiments, low doses of nbUVB can be sufficient to promote melanocyte regeneration. Although higher doses are within the scope of certain embodiments of the invention and may under some circumstances provide benefits, in other embodiments treatment with heretofore sub-clinical dosing can provide benefits and avoid adverse effects associated with more intensive exposure to UV.

In certain embodiments, the JAKi is any known or heretofore unknown JAKi. In other embodiments, the JAKi is at least one selected from the group consisting of:

tofacitinib (3-((3R,4R)-4-methyl-3-(methyl(7H-pyrrolo[2,3-d]pyrimidin-4-yl)amino) piperidin-1-yl)-3-oxo-propanenitrile), ruxolitinib ((R)-3-(4-(7H-pyrrolo[2,3-d]pyrimidin-4-yl)-1H-pyrazol-1-yl)-3-cyclopentyl propanenitrile), oclacitinib (N-Methyl-1-(trans-4-(methyl(7H-pyrrolo[2,3-d]pyrimidin-4-yl)amino) cyclohexyl)methanesulfonamide), baricitinib (2-(3-(4-(7H-pyrrolo[2,3-d]pyrimidin-4-yl)-1H-pyrazol-1-yl)-1-(ethylsulfonyl) azetidin-3-yl)acetonitrile), filgotinib (N-(5-(4-((1,1-dioxidothiomorpholino)methyl)phenyl-[1,2,4]triazolo[1,5-a]pyridin-2-yl)cyclopropane carboxamide), gandotinib (3-(4-chloro-2-fluorobenzyl)-2-methyl-N-(5-methyl-1H-pyrazol-3-yl)-8-(morpholinomethyl)imidazo(1,2-b)pyridazin-6-amine), lestaurtinib (9,12-Epoxy-1H-diindolo[1,2,3-fg:3',2',1'-kl]pyrrolo[3,4-i][1,6]benzodiazocin-1-one, 2,3,9,10,11,12-hexahydro-10-hydroxy-10-(hydroxymethyl)-9-methyl-, (9S,10S,12R)-), momelotinib (N-(cyanomethyl)-4-{2-[4-(morpholin-4-yl)anilino]pyrimidin-4-yl}benzamide), pacritinib (11-(2-pyrrolidin-1-ylethoxy)-14,19-dioxa-5,7,26-triazatetracyclo (19.3.1.1(2,6).1(8,12))heptacosa-1(25),2(26),3,5,8,10,12(27),16,21,23-decaene), upadacitinib (ABT-494, or (3S,4R)-3-ethyl-4-(3H-imidazo[1,2-a]pyrrolo[2,3-e]pyrazin-8-yl)-N-(2,2,2-trifluoroethyl)pyrrolidine-1-carboxamide), peficitinib (4-[[(1R,3S)-5-hydroxy-2-adamantyl]amino]-1H-pyrrolo[2,3-b]pyridine-5-carboxamide), cucurbitacin I (2,16α,20,25-Tetrahydroxy-9-methyl-19-Nor-9β,10α-lanosta-1,5,23-triene-3,11,22-trione), CHZ868 (N-(4-((2-((2,4-difluorophenyl)amino)-1,4-dimethyl-1H-benzo[d]imidazol-5-yl)oxy)pyridin-2-yl)acetamide), fedratinib (Benzenesulfonamide, N-(1,1-dimethylethyl)-3-[[5-methyl-2-[[4-[2-(1-pyrrolidinyl)ethoxy]phenyl]amino]-4-pyrimidinyl]amino]-), cerdulatinib (4-(cyclopropylamino)-2-((4-(4-(ethylsulfonyl)piperazin-1-yl)phenyl)amino) pyrimidine-5-carboxamide)

ATI-50001 (Aclaris Therapeutics's JAKi),

Leo-124429 (LeoPharma's JAKi), or a salt or solvate thereof.

In certain embodiments, the JAKi is tofacitinib, or a salt or solvate thereof. In other embodiments, the JAKi is ruxolitinib, or a salt or solvate thereof.

In certain embodiments, the at least one JAKi is a specific inhibitor to one or more of JAK1, JAK2, JAK3, or tyrosine kinase (Tyk) 2. In other embodiments, the at least one JAKi is a non-specific inhibitor. In embodiments including more than one JAKi, multiple inhibitor types can be utilized. In certain embodiments, the JAKi is administered in a pharmaceutical composition comprising one or more pharmaceutically acceptable excipients. In other embodiments, the JAKi is administered orally. In yet other embodiments, the JAKi is administered topically. In yet other embodiments, topical ruxolitinib is administered to the subject as a 1.5% cream. In yet other embodiments, the JAKi is administered intralesionally. In yet other embodiments, the JAKi is administered subcutaneously.

In certain embodiments, the phototherapy is ultraviolet B (UVB, 280-320 nm) phototherapy. In other embodiments, the phototherapy is narrowband ultraviolet B (nbUVB, 311-312 nm) phototherapy. In yet other embodiments, the phototherapy is ultraviolet A (UVA, 320-340 nm) phototherapy. In yet other embodiments, the phototherapy is ultraviolet A1 (UVA1, 340-400 nm) phototherapy. In yet other embodiments, the phototherapy is visible light (400-700 nm) phototherapy. In yet other embodiments, the phototherapy is a combination of phototherapies, including but not limited to those listed above.

In certain embodiments, the phototherapy comprises a dose that is insufficient for use as a monotherapy for vitiligo, including but not limited to 150 mJ/cm$^2$ of nbUVB or less. In other embodiments, the phototherapy comprises a dose of, in non-limiting embodiments, 50-4000 mJ/cm$^2$ of nbUVB and/or 10-6,000 mJ/cm$^2$ of UVB and/or 0.5-40 J/cm$^2$ of UVA and/or 10-200 J/cm$^2$ of UVA1. In yet other embodiments, the phototherapy has a duration that is insufficient (non-therapeutically effective) for use as a monotherapy for vitiligo, including but not limited to 4 weeks. In yet other embodiments, the phototherapy comprises a number of phototherapy treatments that is insufficient (non-therapeutically effective) for use as a monotherapy for vitiligo, including but not limited to 12 treatments.

In certain embodiments, phototherapy is applied to the subject's entire body. In other embodiments, phototherapy is limited to specific areas of the subject's body, including but not limited to areas of depigmentation. Accordingly, in certain embodiments, phototherapy is delivered by a full body-sized unit or a smaller unit or a handheld device. In yet other embodiments, phototherapy is delivered by controlled or prescribed exposure to sunlight.

In certain embodiments, the at least one JAKi includes other methods for inhibiting the activity of JAK, including but not limited to siRNA, antibodies, isolated peptides or isolated polynucleotides, which bind JAK at the level of protein or nucleic acid and reduce the level of JAK activity or any other known or heretofore unknown method for modulating the activity of JAK.

Kits

In another aspect, the invention comprises a kit comprising an effective amount of at least one JAKi and instructional material comprising instructions for the concomitant administration of the at least one JAKi with phototherapy. In certain embodiments, the JAKi is any of the above described inhibitors. The instructional material can contain any information necessary to allow the practice of the above described method. In particular, the instructional material can include directions and information directing the concomitant administration of the at least one JAKi and phototherapy. Possible means and methods for delivering phototherapy are described elsewhere herein and includes sunlight. In certain embodiments, the kit also includes a UV emitting device for phototherapy. In general, the UV emitting device may be any that a person of skill in the art would recognize as suitable for the purpose.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.1 and 5,000 mg/kg of body weight/per day. The pharmaceutical compositions useful for practicing the invention may be administered to deliver a dose of from 1 ng/kg/day and 100 mg/kg/day. In certain embodiments, the invention envisions administration of a dose which results in a concentration of the compound of the present invention from 1 µM and 10 µM in a mammal. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/ formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation". For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 0.05% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer.

Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically-or naturally derived.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in humans. The dosage of such compounds lies preferably within a range of circulating concentrations that include the ED50 with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods & Materials

This study is a retrospective case series of 10 patients seen between July 2014 and January 2017. Medical records of patients with vitiligo, aged 18 years and older, treated with tofacitinib for at least 3 months were reviewed. Clinical and demographic information, including biological sex, age, disease duration and course, medical history, family history, and prior treatments were collected. Before initiating tofacitinib, all patients underwent baseline laboratory evaluation including comprehensive metabolic panel, complete blood cell count with differential, fasting lipid panel, QuantiF-ERON-TB Gold® (Cellestis Limited, Melbourne, Australia), and screening for HIV and hepatitis B and C. Body surface area (BSA) of depigmentation was assessed prior to and at the end of treatment. Serial laboratory monitoring, physical exams, and review of systems were used to monitor for adverse events. Suction blister sampling was performed in one patient before beginning tofacitinib and then again 10 months later to assess changes in T cell recruitment and chemokine expression. Three sites were selected for sampling—one was a site of vitiligo that did not previously respond to treatment with tofacitinib, one was a recently active site (featuring confetti depigmentation) that previously responded to tofacitinib, and one was unaffected skin.

Suction Blister Sampling and Processing

The Negative Pressure Instrument Model NP-4 (Electronic Diversities®, Finksburg, MD) was used to induce suction blisters (1 cm in diameter). Blisters formed at a pressure between 10-15 mm Hg negative pressure and at a constant temperature of 40° C. Once blisters formed, the blister fluid was aspirated 135 through the roof using a 1 mL insulin syringe. Cells in the blister fluid were pelleted at 330×g for 10 minutes and prepared for flow cytometry. The supernatant of the blister fluid was stored at −80° C. until analysis by enzyme-linked immunosorbent-assays (ELISA) for chemokines. None of the blisters were hemorrhagic.

ELISA

Chemokines were assayed using the Human CXLC9/MIG DuoSet ELISA (DY392) and Human CXCL10/IP-10 Duo-Set ELISA (DY266, R&D Systems) per the manufacturer's instructions. Optical densities were measured using a Perkin Elmer EnVision 2102® multilabel reader and analyzed using a 4 parameter logarithmic standard curve.

Flow Cytometry

Cells were blocked with Human TruStain and incubated with an antibody cocktail for 30 minutes at 4° C. Anti-human CD45 (2D1) and CD8 (SK1) were used at 1:20 dilution. Anti-human CD3 (OKT3) was used at 1:200 dilution (BioLegend) and Fixable Viability Dye eFluor 455UV at 1:1000 (Ebioscience). Prior to cell staining in the PBMCs, $10^6$ PBMCs were treated with desatinib for 30 minutes at 36° C., pelleted and incubated with Mart-1 Pentamer (Pro-Immune, 082) for 10 minutes at room temperature.

Example 1

Patient characteristics

All 10 patients in this case series were adults. Duration of disease was 4-33 years (mean 16.6, SD, standard deviation, 8.8). Eight patients had generalized vitiligo and 2 patients had primarily acral involvement, with 1-100% BSA. Additional patient characteristics are described in Table 1. Previous treatments included nbUVB (9 patients), topical calcineurin inhibitors (7), topical steroids (4), psoralen with ultraviolet A (4), excimer laser (2), blister grafting (1), cryotherapy (1), Fraxel laser (1), pseudocatalase cream (1), prednisone (1), and secukinumab (1).

TABLE 1

Clinical characteristics of patients

| Patient No. | Age | Sex | Race | BSA Prior to tofacitinib | BSA after to tofacitinib | Tofacitinib treatment duration (months) | Vitiligo disease duration (years) | Responder Status |
| --- | --- | --- | --- | --- | --- | --- | --- | --- |
| 1 | 54 | F | Caucasian | 10% | 4% | 10 | 4 | R |
| 2 | 45 | M | Caucasian | 28% | 24% | 8 | 23 | R |
| 3 | 46 | F | Caucasian | 39% | 24% | 11 | 16 | R |
| 4 | 55 | F | Caucasian | 10% | 8% | 14 | 24 | R |
| 5 | 45 | M | East Indian | 2% | 2%* | 10 | 5 | R |
| 6 | 28 | M | Caucasian | 7% | 7% | 3 | 14 | NR |
| 7 | 47 | F | Hispanic | 1% | 1% | 9 | 18 | NR |
| 8 | 49 | M | Caucasian | 4% | 4% | 15 | 17 | NR |
| 9 | 32 | M | Hispanic | 6% | 6% | 4 | 12 | NR |
| 10 | 73 | F | Caucasian | 100% | 100% | 11 | 33 | NR |

BSA, body surface area;
R, responder;
NR, non-responder
*Islands of repigmentation, apparent after 12 treatments with nbUVB phototherapy did not change the BSA appreciably at this early time point.

Clinical Course and Results

Ten patients underwent treatment with tofacitinib 5-10 mg QD-BID for an average of 9.5 months (SD 3.8, range 3-15). A mean decrease of 5.4% BSA involvement with vitiligo was observed in 5/10 patients, while the other 5 patients did not achieve any repigmentation. In the 5 patients who achieved some reversal of disease, repigmentation occurred only in sun-exposed areas of skin in 3 of them, diffusely in another patient undergoing concomitant full-body nbUVB phototherapy, and to the dorsal hands in another patient after starting concomitant hand nbUVB phototherapy.

Patient 1 is a 45-year-old Caucasian female who had generalized vitiligo affecting approximately 10% BSA. She had previously been treated with tofacitinib 5 mg daily and, over 5 months, experienced near complete repigmentation of her face, forearms, and dorsal hands, with only minimal repigmentation at other body sites, including the trunk. Subsequently, she stopped tofacitinib for 8 months and, during this period, depigmentation recurred in the areas that had previously responded. Prior to re-treatment with tofacitinib and again after 10 months of treatment, she underwent suction blister sampling in order to evaluate the effect of this treatment on vitiligo pathogenesis.

Treatment with tofacitinib 5 mg daily over 6 months, started in late spring, again led to repigmentation of the face, forearms and dorsal hands, and the upper back and shoulders, but not the lower back or other sun-protected body sites.

Patient 2 is a 45-year-old Caucasian male who had generalized vitiligo affecting approximately 28% BSA. In his occupation as an athletics coach, his days were spent in the sun, usually wearing shorts and short-sleeved shirts. Treatment with tofacitinib 5 mg twice daily, started in early spring, led to partial repigmentation of the face, lateral and posterior neck, and forearms over 3 months. After 8 months of treatment, near-complete repigmentation was noted on the face, neck (but not in the submental area), and forearms, as well as islands of repigmentation involving the dorsal hands and lower legs; sun-protected body sites, however, remained unchanged. Repigmentation was maintained while taking tofacitinib during the winter, when sunlight exposure was minimal.

Patient 3 is a 46-year-old Caucasian female who had generalized vitiligo affecting approximately 39% BSA. She reported some repigmentation with nbUVB in the past, but out of concern for skin cancer, she decreased the dose and had been treating herself at a dose of 150 mJ every other day with no improvement, and this was continued without modification after initiation of tofacitinib 5 mg twice daily. After 11 months of treatment, complete repigmentation of the face and >75% repigmentation of the back was observed, and innumerable islands of repigmentation involving all other body sites were apparent.

Patient 4 is a 55-year-old Caucasian female who had generalized vitiligo affecting approximately 10% BSA. After 14 months of therapy, near-complete repigmentation of the face was noted; neither the hands nor sun-protected body sites, however, showed evidence of repigmentation.

Patient 5 is a 45-year-old East Indian male who had vitiligo affecting his dorsal hands, elbows, lower back, and buttocks. He wore dark brown makeup on his hands to disguise the white patches. His vitiligo had been unresponsive to tofacitinib 5-10 mg twice daily for 1 year when he initiated concomitant nbUVB hand phototherapy, and, after approximately 12 treatments (most recent dose 350 mJ), islands of repigmentation were apparent.

Of the remaining 5 patients, who did not experience repigmentation, only one reported significant sunlight exposure, and the others either avoided sunlight or practiced photoprotection.

Adverse Events

The most common side effect was upper respiratory infection in 2 patients. One patient reported weight gain of 5 pounds and one patient reported arthralgias. Mild elevations of lipids were noted in 4 patients. There were no serious adverse events.

Suction Blister Sampling

Previous analysis of suction blisters of active vitiligo lesions demonstrated that T cell number and CXCL9 protein level were both sensitive and specific to predict disease activity. This method was used to measure the treatment response of patient 1. Prior to re-treatment with tofacitinib, she underwent suction blister sampling of a treatment unresponsive site (intermammary chest), a treatment-responsive site (forearm), and skin unaffected by vitiligo (arm). After 10 months of tofacitinib, she underwent blister sampling again at the same sites.

Figure 1A:
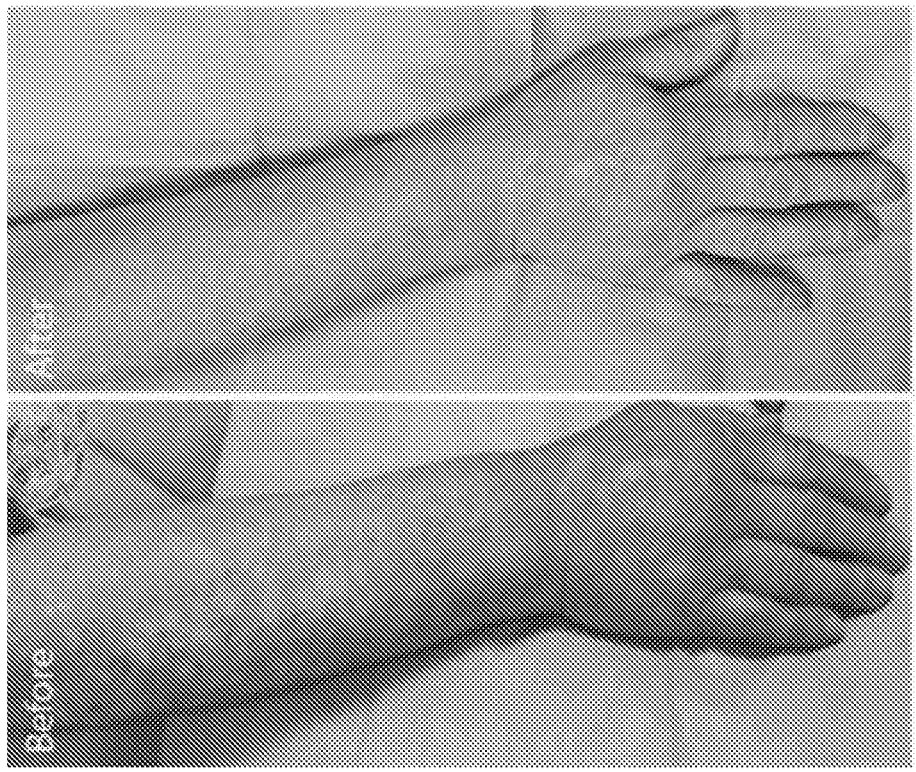
Figure 2A:
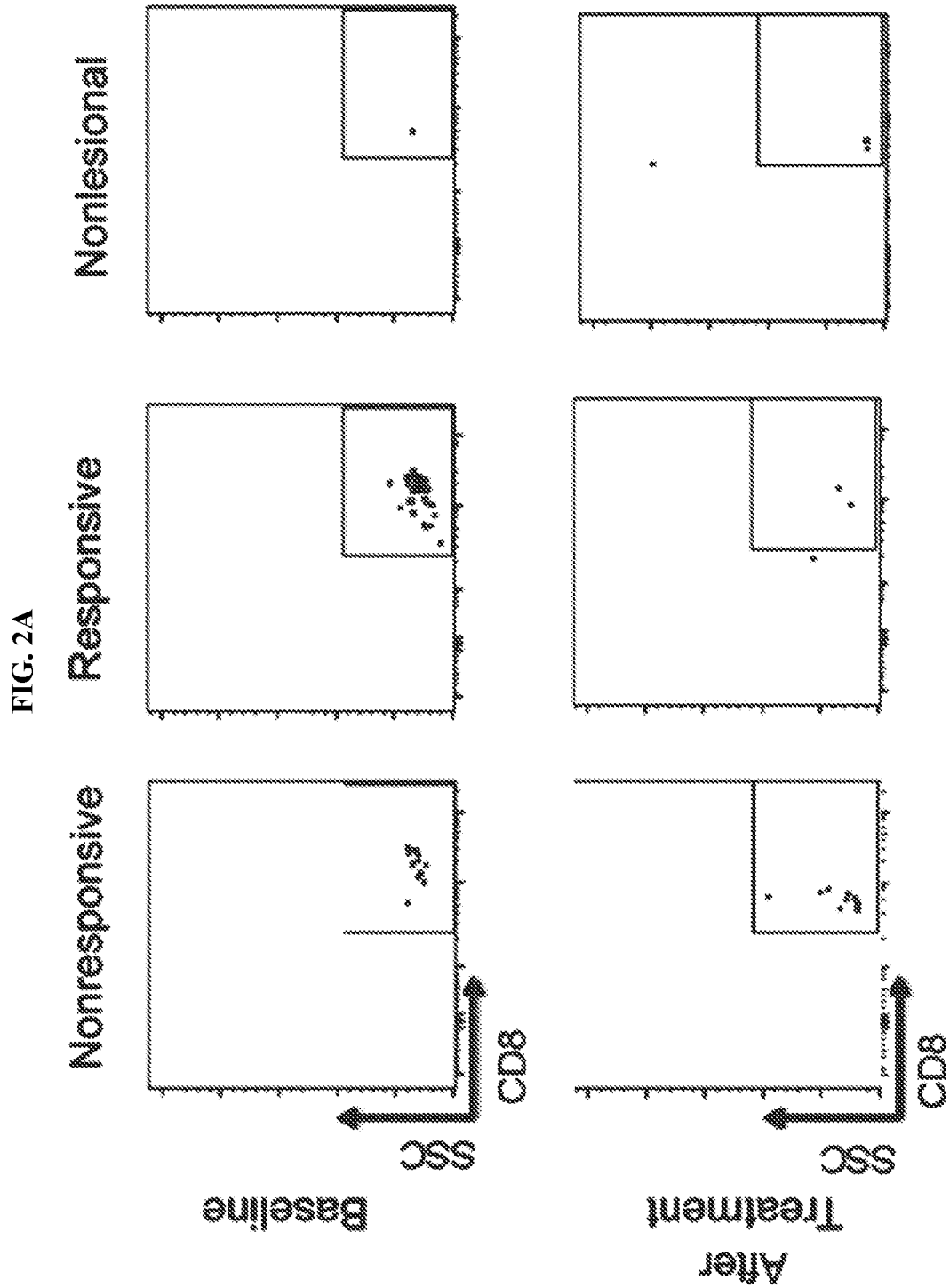
FIGS. 2A-2D depict CD8⁺ T cell quantification and chemokine protein levels in blister fluid in patient 1 in Example 1.
Figure 2B:
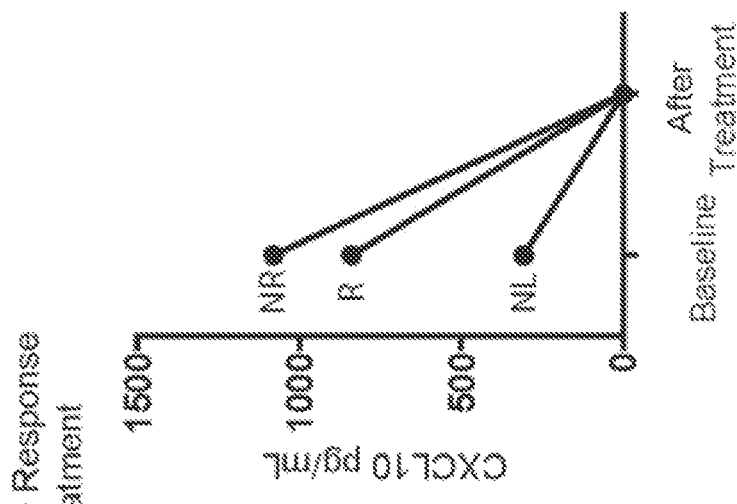

A small number of T cells was detected in all sites at baseline as well as during treatment. At baseline, there were 29 $CD8^+$ T cells in the previously non-responding lesion and a greater number in the recently developed lesion (69 cells). Both lesional sites had more cells than in unaffected skin. Following treatment with tofacitinib, absolute numbers in each site were reduced (FIGS. 2A and 2B). Similarly, melanocyte-specific T cells (HLA pentamer positive) were detected in the PBMCs at baseline, and this percentage did not change with tofacitinib treatment, and even increased slightly (FIG. 1A).

Figure 2C:
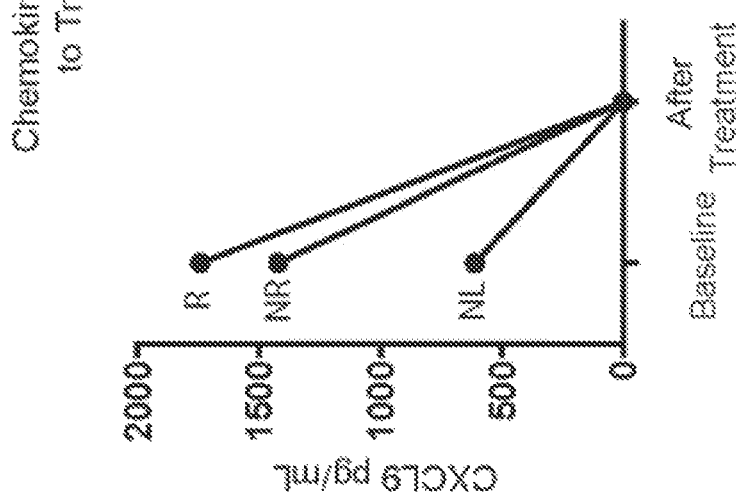
Figure 2D:
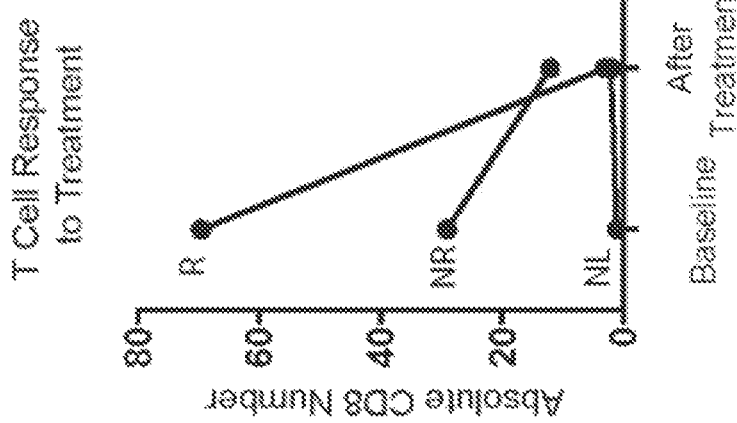
Figure 4B:
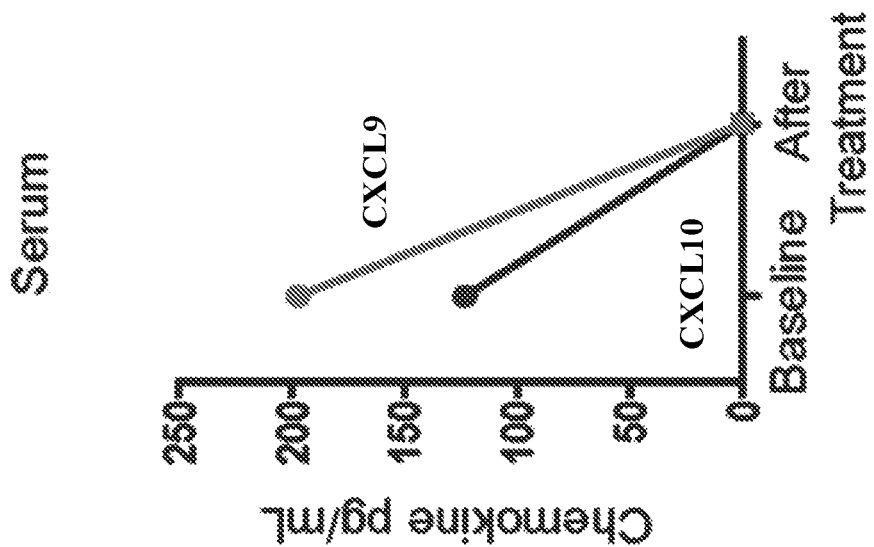
FIGS. 4A-4B depict data from the study described herein.
Figure 4A:
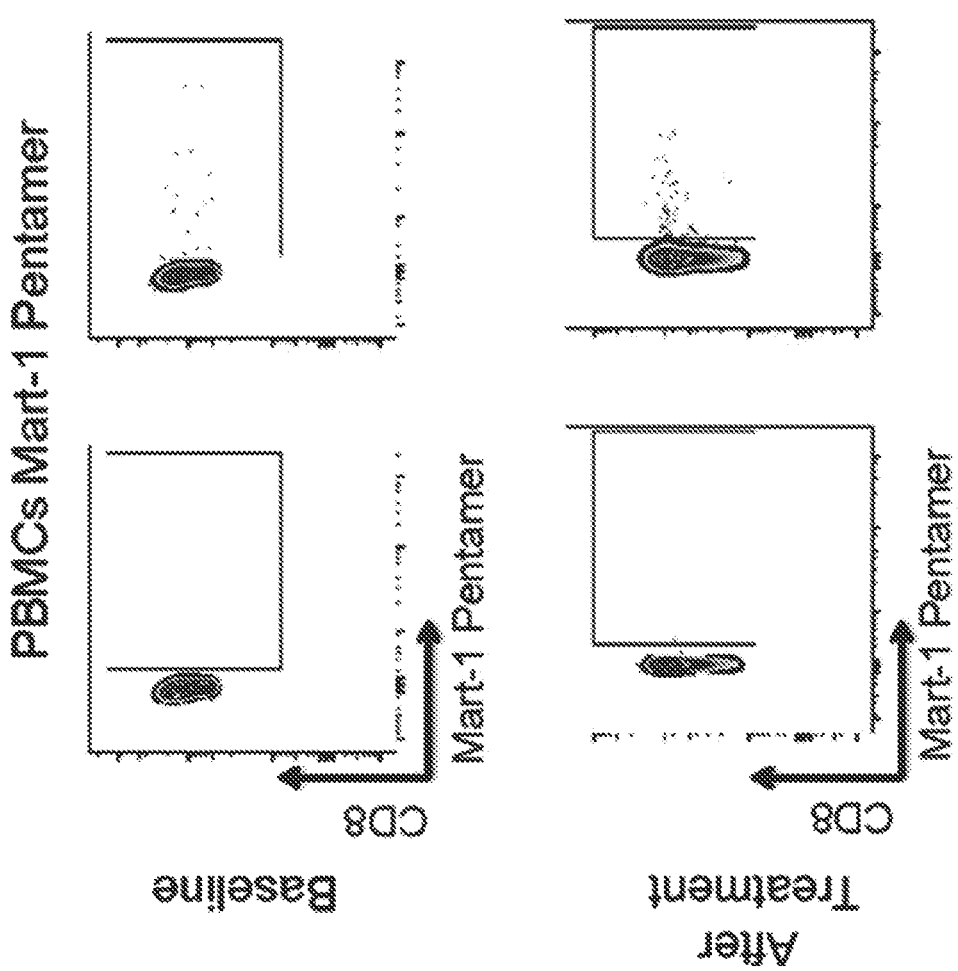

CXLC9 was elevated in all 4 lesional sites compared to unaffected skin at baseline (FIG. 2, panel C), and CXCL10 was elevated in 3 of 4 lesional sites (FIG. 2D). Following treatment, chemokine levels became undetectable in both the blister fluid (FIGS. 2C-2D) and serum (FIG. 4B).

In summary, tofacitinib effectively decreased T cell numbers and chemokine proteins (a measure of IFN-γ signaling) in the skin. In the blood, tofacitinib did not affect the number of autoreactive T cells but did decrease chemokines.

Example 2

Figure 5A:
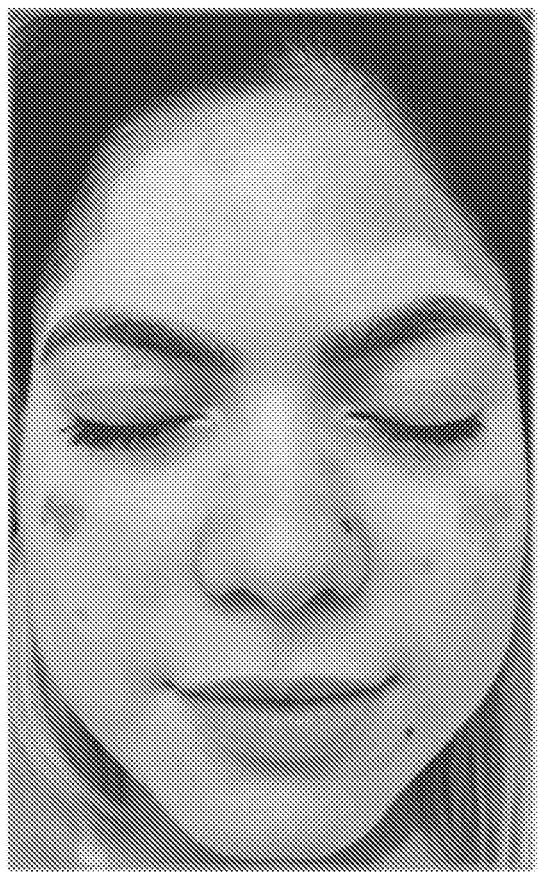
FIGS. 5A-5B depict images of the patient discussed in Example 2, case 1, before (FIG. 5A) and after (FIG. 5B) treatment with tofacitinib and low-dose, narrowband UV-B Phototherapy.
Figure 5B:
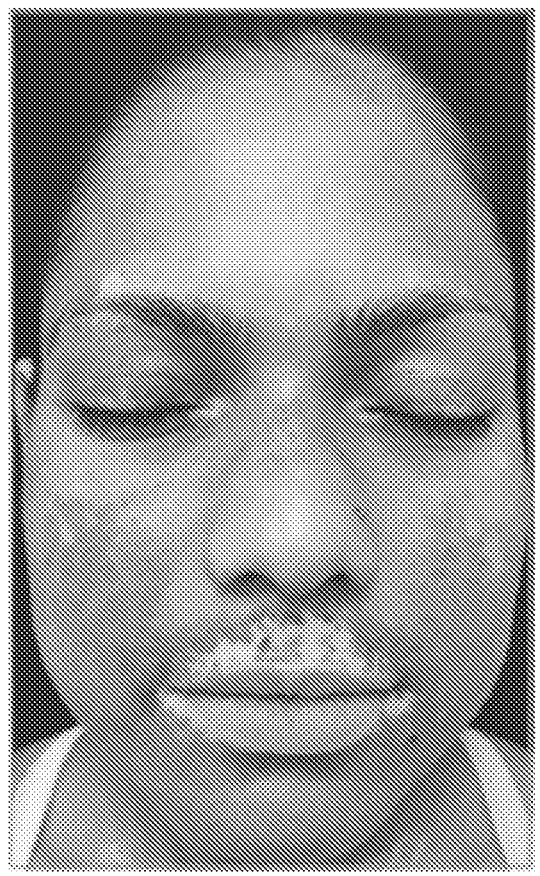

Case 1. A Hispanic woman in her 30s presented with a 12-year history of vitiligo. Facial lesions appeared during her first pregnancy and spread over the following year to her neck, torso, and extremities. Her family history was unremarkable. Treatment with liquid nitrogen and topical corticosteroids had been unsuccessful, and a 3-month course of topical MBEH failed to induce depigmentation. On physical examination, there were white patches involving about 75% of her face (FIG. 5A) as well as white patches on the neck, chest, forearms, hands, and shins. Treatment was begun with tofacitinib, 5 mg, twice daily and full-body narrowband UV-B (400-500 mJ) twice weekly. After 3 months of treatment, there was nearly complete repigmentation of her face (FIG. 5B), 75% or greater repigmentation of her neck, chest, forearms, and shins, and only minimal freckling of the dorsal hands.

Case 2. A white man in his 50s presented with long-standing vitiligo. Treatment with topical corticosteroids, topical calcineurin inhibitors, excimer laser, and narrowband UV-B had been unsuccessful. Four years prior to presentation, he had achieved depigmentation of the face using topical MBEH. On physical examination, there were white patches involving about 90% of his face as well as white patches on the torso and arms. Treatment was begun with tofacitinib, 5 mg, twice daily and narrowband UV-B (360-500 mJ) 2 to 3 times weekly to only the face. After 3 months of treatment, there was about 50% repigmentation of the face, and, after 6 months, about 75% facial repigmentation. No repigmentation occurred at the other body sites.

Both patients have continued this treatment regimen, and at last follow-up there were no adverse effects, and complete blood cell count, liver function tests, serum creatinine, and fasting lipids revealed no abnormalities.

In the present cases, treatment of 2 patients with vitiligo with significant facial involvement using a combination of tofacitinib and low-dose, narrowband UV-B led to rapid repigmentation in both. The results support the hypothesis that photoactivation is required to stimulate melanocytes to leave their stem cell niche and seed the epidermis, while tofacitinib suppresses the autoimmune response. In contrast to narrowband UV-B monotherapy, repigmentation using narrowband UV-B together with tofacitinib required relatively low-dose light exposure. Repigmentation in patient 2 is particularly interesting and unexpected given his prior successful depigmentation with MBEH. Without wishing to be limited by any theory, this result suggests that melanocytes of the interfollicular epidermis, but not melanocyte stem cells, are destroyed by MBEH. Combination therapy with JAK inhibitors and low-dose, narrowbandUV-Bmay be effective targeted treatment for vitiligo.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating vitiligo in a subject, the method comprising:
    administering phototherapy and a therapeutically effective amount of at least one Janus kinase inhibitor to the subject,
    wherein the phototherapy comprises a dose of narrow band UVB (nbUVB) radiation that is equal to or less than 150 mJ/cm$^2$, and
    wherein the intensity, duration, or frequency of the phototherapy used is ineffective in treating vitiligo in a subject who is not being co-administered the at least one Janus kinase inhibitor.

2. The method of claim 1, wherein the at least one Janus kinase inhibitor is selected from the group consisting of tofacitinib, ruxolitinib, oclacitinib, baricitinib, filgotinib, gandotinib, lestaurtinib, momelotinib, pacritinib, upadacitinib (ABT-494), peficitinib, cucurbitacin I, CHZ868, fedratinib, cerdulatinib, ATI-50001, and Leo-124429, or a salt or solvate thereof.

3. The method of claim 1, wherein the at least one Janus kinase inhibitor is tofacitinib, or a salt or solvate thereof.

4. The method of claim 3, wherein the subject is administered 5-20 mg/day of tofacitinib.

5. The method of claim 1, wherein the at least one Janus kinase inhibitor is ruxolitinib, or a salt or solvate thereof.

6. The method of claim 5, wherein the subject is administered 5-50 mg/day of ruxolitinib.

7. The method of claim 1, wherein the phototherapy is applied at least to the subject's skin section that is afflicted by vitiligo.

8. The method of claim 1, wherein the phototherapy is applied only to the subject's skin section that is afflicted by vitiligo.

9. The method of claim 1, wherein the at least one Janus kinase inhibitor is administered topically to the subject.

10. The method of claim 1, wherein the at least one Janus kinase inhibitor is administered orally to the subject.

11. The method of claim 1, wherein the subject continues to be administered the at least one Janus kinase inhibitor after the phototherapy is discontinued.

12. The method of claim 1, wherein the at least one Janus kinase inhibitor is part of a pharmaceutical composition further comprising at least one pharmaceutically acceptable carrier.

13. A kit comprising an effective amount of at least one Janus kinase inhibitor and instructional material comprising instructions for the concomitant administration of the at least one Janus kinase inhibitor with phototherapy to treat vitiligo in a subject,
- wherein the phototherapy comprises a dose of narrow band UVB (nbUVB) radiation that is equal to or less than about 150 mJ/cm$^2$, and
- wherein the intensity, duration, or frequency of the phototherapy used is ineffective in treating vitiligo in a subject who is not being co-administered the at least one Janus kinase inhibitor.

14. The kit of claim 13, wherein the at least one Janus kinase inhibitor is tofacitinib.

15. The kit of claim 13, wherein the Janus kinase inhibitor is ruxolitinib.

16. The kit of claim 13, further comprising a handheld phototherapy device.

* * * * *